United States Patent
Collins et al.

(10) Patent No.: US 7,462,345 B2
(45) Date of Patent: *Dec. 9, 2008

(54) RADIONUCLIDE LABELING OF VITAMIN $B_{12}$ AND COENZYMES THEREOF

(75) Inventors: Douglas A. Collins, Rochester, MN (US); Henricus Petrus Cornelius Hogenkamp, Roseville, MN (US)

(73) Assignees: Mayo Foundation for Medical Education and Research, Rochester, MN (US); Regents of the University of Minnesota, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/603,297

(22) Filed: Nov. 20, 2006

(65) Prior Publication Data

US 2007/0110667 A1    May 17, 2007

Related U.S. Application Data

(60) Continuation of application No. 10/620,273, filed on Jul. 15, 2003, now Pat. No. 7,141,233, which is a division of application No. 09/626,213, filed on Jul. 26, 2000, now Pat. No. 6,613,305, which is a division of application No. 09/354,553, filed on Jul. 15, 1999, now Pat. No. 6,096,290, which is a division of application No. 09/059,227, filed on Apr. 13, 1998, now Pat. No. 6,004,533, which is a division of application No. 08/557,955, filed on Nov. 13, 1995, now Pat. No. 5,739,313.

(51) Int. Cl.
*A61K 51/00*    (2006.01)

(52) U.S. Cl. .................... 424/1.73; 424/1.11; 424/1.65; 424/9.1

(58) Field of Classification Search ................ 424/1.11, 424/1.65, 1.69, 1.73, 1.49, 1.81, 1.85, 1.89, 424/9.1; 534/7, 10–16; 514/2, 10; 536/26.4, 536/26.44
See application file for complete search history.

(56) References Cited

U.S. PATENT DOCUMENTS

| | | |
|---|---|---|
| 3,494,769 A | 2/1970 | Tressler |
| 3,627,788 A | 12/1971 | Bouchaudon et al. |
| 3,936,440 A | 2/1976 | Nath |
| 3,981,863 A | 9/1976 | Niswender et al. |
| 4,209,614 A | 6/1980 | Bernstein et al. |
| 4,279,859 A | 7/1981 | Gutcho et al. |
| 4,283,342 A | 8/1981 | Yolles |
| 4,301,140 A | 11/1981 | Frank et al. |
| 4,399,163 A | 8/1983 | Brennan et al. |
| 4,411,925 A | 10/1983 | Brennan et al. |
| 4,423,029 A | 12/1983 | Rizzi |
| 4,465,775 A | 8/1984 | Houts |
| 4,959,356 A | 9/1990 | Miura |
| 4,976,960 A | 12/1990 | Grossman et al. |
| 4,987,071 A | 1/1991 | Cech et al. |
| 5,057,301 A | 10/1991 | Wilbur |
| 5,187,107 A | 2/1993 | Watkins et al. |
| 5,286,853 A | 2/1994 | Spielvogel |
| 5,308,606 A | 5/1994 | Wilson et al. |
| 5,372,808 A | 12/1994 | Blatt |
| 5,405,598 A | 4/1995 | Schinazi et al. |
| 5,405,839 A | 4/1995 | Toraya et al. |
| 5,428,023 A | 6/1995 | Russell-Jones et al. |
| 5,449,720 A | 9/1995 | Russell-Jones et al. |
| 5,462,724 A | 10/1995 | Schinazi et al. |
| 5,548,064 A | 8/1996 | Russell-Jones et al. |
| 5,556,644 A | 9/1996 | Chandra |
| 5,569,477 A | 10/1996 | Nesbitt |

(Continued)

FOREIGN PATENT DOCUMENTS

DE    1 811 518    11/1968

(Continued)

OTHER PUBLICATIONS

U.S. Appl. No. 60/129,733, filed Apr. 16, 1999.

(Continued)

*Primary Examiner*—D. L Jones
(74) *Attorney, Agent, or Firm*—Fish & Richardson P.C.

(57) ABSTRACT

A compound useful for in vivo imaging of organs and tumors is provided of formula:

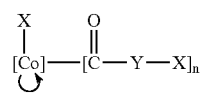

wherein

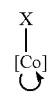

is a cobalamin,

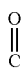

is derived from a corrin carboxylic acid group of said cobalamin, Y is a linking group and X is a chelating group, optionally comprising a detectable radionuclide or a paramagnetic metal ion, and n is 1-3.

25 Claims, 2 Drawing Sheets

U.S. PATENT DOCUMENTS

| | | | |
|---|---|---|---|
| 5,574,018 A | 11/1996 | Habberfield et al. | |
| 5,578,336 A | 11/1996 | Monte | |
| 5,589,463 A | 12/1996 | Russell-Jones et al. | |
| 5,599,796 A | 2/1997 | Schinazi et al. | |
| 5,608,060 A | 3/1997 | Axworthy et al. | |
| 5,630,786 A | 5/1997 | Griffin et al. | |
| 5,736,292 A | 4/1998 | Ida et al. | |
| 5,739,313 A * | 4/1998 | Collins et al. | 536/26.44 |
| 5,807,832 A | 9/1998 | Russell-Jones et al. | |
| 5,820,903 A | 10/1998 | Fleury et al. | |
| 5,840,880 A | 11/1998 | Morgan, Jr. et al. | |
| 5,869,084 A | 2/1999 | Paradissis | |
| 5,869,465 A | 2/1999 | Morgan, Jr. et al. | |
| 5,869,466 A | 2/1999 | Russell-Jones et al. | |
| 5,872,107 A | 2/1999 | Schinazi et al. | |
| 5,877,165 A | 3/1999 | Miura et al. | |
| 5,879,465 A | 3/1999 | McKevitt et al. | |
| 5,925,377 A | 7/1999 | Gerth et al. | |
| 5,925,625 A | 7/1999 | Merkus | |
| 5,936,082 A | 8/1999 | Bauer | |
| 5,948,443 A | 9/1999 | Riley et al. | |
| 5,955,321 A | 9/1999 | Bijl | |
| 5,964,224 A | 10/1999 | Kaji | |
| 5,985,339 A | 11/1999 | Kamarei | |
| 6,004,533 A * | 12/1999 | Collins et al. | 424/1.73 |
| 6,017,902 A | 1/2000 | Glass | |
| 6,022,853 A | 2/2000 | Kuberasampath | |
| 6,030,650 A | 2/2000 | Kamarei | |
| 6,039,978 A | 3/2000 | Bangs et al. | |
| 6,056,973 A | 5/2000 | Allen et al. | |
| 6,071,545 A | 6/2000 | Hendler | |
| 6,074,625 A | 6/2000 | Hawthorne et al. | |
| 6,077,557 A | 6/2000 | Gordon et al. | |
| 6,083,926 A | 7/2000 | Morgan et al. | |
| 6,093,425 A | 7/2000 | Kamarei | |
| 6,093,701 A | 7/2000 | Wolff et al. | |
| 6,096,290 A * | 8/2000 | Collins et al. | 424/1.65 |
| 6,110,472 A | 8/2000 | Levere et al. | |
| 6,121,249 A | 9/2000 | Weissmann et al. | |
| 6,126,980 A | 10/2000 | Smith et al. | |
| 6,150,341 A | 11/2000 | Russell-Jones et al. | |
| 6,153,737 A | 11/2000 | Manoharan et al. | |
| 6,159,502 A | 12/2000 | Russell-Jones et al. | |
| 6,159,734 A | 12/2000 | McKay et al. | |
| 6,165,720 A | 12/2000 | Felgner | |
| 6,165,789 A | 12/2000 | Monia et al. | |
| 6,180,766 B1 | 1/2001 | Schinazi et al. | |
| 6,183,723 B1 | 2/2001 | Seetharam et al. | |
| 6,211,355 B1 * | 4/2001 | Collins et al. | 536/26.41 |
| 6,214,535 B1 | 4/2001 | Matsumori | |
| 6,221,397 B1 | 4/2001 | Russell-Jones et al. | |
| 6,262,253 B1 | 7/2001 | Russell-Jones et al. | |
| 6,274,564 B1 | 8/2001 | Sarill et al. | |
| 6,291,184 B1 | 9/2001 | Gold et al. | |
| 6,315,978 B1 | 11/2001 | Grissom et al. | |
| 6,395,492 B1 | 5/2002 | Manoharan et al. | |
| 6,613,305 B1 * | 9/2003 | Collins et al. | 424/1.73 |
| 6,806,363 B1 * | 10/2004 | Collins et al. | 536/26.4 |
| 6,838,073 B1 * | 1/2005 | Collins et al. | 424/1.69 |
| 6,905,884 B2 | 6/2005 | Grissom | |
| 6,962,906 B2 | 11/2005 | Efimov | |
| 7,141,233 B2 * | 11/2006 | Collins et al. | 424/9.1 |
| 7,179,445 B2 * | 2/2007 | Collins et al. | 424/1.69 |
| 2002/0002146 A1 | 1/2002 | Halevie-Goldman | |
| 2002/0042394 A1 | 4/2002 | Hogenkamp et al. | |
| 2002/0049155 A1 | 4/2002 | Hogenkamp | |
| 2002/0151525 A1 | 10/2002 | Collins et al. | |
| 2003/0018009 A1 | 1/2003 | Collins | |
| 2003/0144198 A1 | 7/2003 | Collins | |
| 2004/0162240 A1 | 8/2004 | Collins et al. | |
| 2005/0004010 A1 | 1/2005 | Collins et al. | |

FOREIGN PATENT DOCUMENTS

| | | |
|---|---|---|
| EP | 0 005 834 | 12/1979 |
| EP | 0 069 450 | 4/1985 |
| EP | 0 220 030 | 10/1986 |
| EP | 0 165 716 | 1/1990 |
| EP | 0 506 242 | 12/1998 |
| ES | 2 088 364 | 8/1996 |
| ES | 2 088 374 | 8/1996 |
| JP | 58-046027 | 9/1981 |
| WO | WO 89/01475 | 2/1989 |
| WO | WO92/09610 | 6/1992 |
| WO | WO 92/13571 | 8/1992 |
| WO | WO 94/27613 | 12/1994 |
| WO | WO 94/27641 | 12/1994 |
| WO | WO 95/27723 | 10/1995 |
| WO | WO96/04016 | 2/1996 |
| WO | WO 96/31243 | 10/1996 |
| WO | WO 97/14711 | 4/1997 |
| WO | WO 97/18231 | 5/1997 |
| WO | WO97/33627 | 9/1997 |
| WO | WO 98/08859 | 3/1998 |
| WO | WO99/29302 | 6/1999 |
| WO | WO 99/65529 | 12/1999 |
| WO | WO 99/65930 | 12/1999 |
| WO | WO 00/62808 | 4/2000 |
| WO | WO00/25793 | 5/2000 |
| WO | WO 00/25793 | 5/2000 |
| WO | WO 00/45857 | 8/2000 |
| WO | WO00/74721 | 12/2000 |
| WO | WO01/00646 | 1/2001 |
| WO | WO 01/28592 | 4/2001 |
| WO | WO 01/28595 | 4/2001 |
| WO | WO 01/30967 | 5/2001 |
| WO | WO01/53311 | 7/2001 |
| WO | WO 01/17694 | 12/2001 |
| WO | WO 01/92283 | 12/2001 |
| WO | WO 01/92288 | 12/2001 |
| WO | WO 02/42318 | 5/2002 |
| WO | WO 02/055530 | 7/2002 |
| WO | WO 03/000010 | 1/2003 |
| WO | WO 03/025139 | 3/2003 |

OTHER PUBLICATIONS

U.S. Appl. No. 60/159,753, filed Oct. 15, 1999.
U.S. Appl. No. 60/159,873, filed Oct. 15, 1999.
U.S. Appl. No. 60/159,874, filed Oct. 15, 1999.
Breeman et al., "Indium-111 labeled DTPA- and DOTA-bombesin analogs for receptor scintigraphy and radiotherapy," *Proc. 46th Annual Meeting of the Society of Nuclear Medicine*, Los Angeles, CA, Jun. 6-10, 1999, Abstract No. 418.
Cannon et al. "Synthesis and Uptake of a Radiolabeled Cobalamin Bioconjugate," *9th International Symposium on Recent Advances in Drug Delivery Systems*, Feb. 1999, pp. 230-231.
Collins et al., "Biodistribution of Radiolabeled Adenosylcobalamin in Patients Diagnosed with Various Malignancies," *Mayo Clin. Proc.*, 2000, 75:568-580.
Cuoto, "Management of Complications of Cancer Chemotherapy," "Chemotherapeutic Agents Commonly used in Veterinary Medicine," *Vet Clin North Am*, 1990, 20(4):1037-1053.
"Current Status of Neutron Capture Therapy," *International Atomic Energy Agency*, May 2001.
DeJong et al., "Radionuclide therapy using radiolabeled somatostatin analogs in tumor-bearing rats," *Proc. 46th Annual Meeting of the Society of Nuclear Medicine*, Los Angeles, CA, Jun. 6-10, 1999, Abstract No. 414.
Gennaro, *Remington: The Science and Practice of Pharmacy*, 1995, 19th edition, vol. 2, pp. 1527-1529, 1561.
Good and Nielsen, "Antisense inhibition of gene expression in bacteria by PNA targeted to mRNA," *Nat. Biotech.*, 1998, 16:355-358.

Guy et al., "Evaluation of coupling of cobalamin to antisense oligonucleotides by thin-layer and reversed-phase liquid chromatography," *J. Chromatog. B*, 1998, 706:149-156.

Hogenkamp, et al., "Chemical synthesis and properties of analogs of adenosylcobalamin," *Biochem.* 1974, 13(13):2736-2740.

Knudsen and Nielsen, "Application of peptide nucleic acid in cancer therapy," *Anti-Cancer Drug*, 1997, 8:113-118.

Kollmer et al., *Int. J. Apl. Radiation Isotopes*, 1974, 25(6):284-285.

Larrea et al., "Tumor necrosis factor alpha gene expression and the response to interferon in chronic hepatitis C," *Hepatology*, 1996, 23:210-217.

Luo et al., Studies on bone tumor therapeutic . . . , *Proc. 46th Annual Meeting of the Society of Nuclear Medicine*, Los Angeles, CA, Jun. 6-10, 1999, Abstract No. 1386.

Merck Index pp. 1577 and 1710, date not available.

Morita et al., "2'-O,4'-C-ethylene-bridged nucleic acids (ENA): highly nuclease-resistant and thermodynamically stable oligonucleotides for antisense drug," *Bioorg. Med. Chem. Lett.*, 2002, 12:73-76.

Nielsen et al., "Sequence-selective recognition of DNA by strand displacement with a thymine-substituted polyamide," *Science*, 1991, 254:1497-1500.

Pathare et al., "Synthesis of Cobalamin Biotin Conjugates That Vary in the Position of Cobalamin Coupling. Evaluation of Cobalamin Derivative Binding to Transcobalamin II," *Bioconj. Chem.*, 1996, 7(2):217-232.

Pinson et al., "Synthesis of Two Doxorubicin-Cobalamin Bioconjugates," 9th International Symposium on Recent Advances in Drug Delivery Systems, Feb. 1999, pp. 228-229.

Purdue University School of Veterinary Medicine, "Chemotherapy Drugs to Know," MCMP 611, Spring 1997, http://www.vet.purdue.edu/bms/courses/mcmp611/chmrx/drg2no61.htm, accessed Nov. 14, 2000.

Russell-Jones et al., "Vitamin B 12 mediated oral delivery systems for granulocyte-colony stimulating factor and erythropoietin," *Bioconj. Chem.*, 1995, 6(4):459-465.

Smeltzer et al., "Cytotoxicities of Two New Cobalamin Bioconjugates," 9th International Symposium on Recent Advances in Drug Delivery Systems, Feb. 1999, pp. 232-233.

Swanson et al., *Pharmaceuticals in Medical Imaging*, 1990, pp. 621-628.

Takakura and Hashida, "Macromolecular drug carrier systems in cancer chemotherapy" macromolecular prodrugs, *Crit. Rev. Oncology: Hematology*, 1995, 18:207-231.

Wahlestedt et al., "Potent and nontoxic antisense oligonucleotides containing locked nucleic acids," *Proc. Natl. Acad. Sci. USA*, 2000, 97(10):5633-5638.

Walker et al., "The chemical synthesis and nuclear magnetic resonance spectroscopy of adenosylcobalamin selectively enriched with carbon-13," *Biochem.*, 1974, 13(12):2650-2655.

Wunderbaldinger et al., "New approaches for imaging in gene therapy," *Eur. J. Radiol.*, 2000, 34(3):156-165.

Yong, "In Vitro and In Vivo Evaluation of o-Carboranylalanine as a Potential Boron Delivery Agent for Neutron Capture Therapy," *Anticancer Research*, 1995, 15:2033-2038.

Akine et al., "Neutron-capture therapy of murine ascites tumor with gadolinium-containing microcapsules," *J. Cancer Res. Clin. Oncol.*, 1992, 119(2):71-73.

Alam et al., "Boronated compounds for neutron capture therapy," *Strahlenther. Onkol.*, 1989, 165:121-123.

Allen, "Human Vitamin B12 Transport Proteins," *Proc. Hematol.*, 1975, 9:57-84.

Allen and Mehlman, "Isolation of Gastric Vitamin B12-binding Proteins Using Affinity Chromatography. I. Purification and properties of human intrinsic factor," *J. Biol. Chem.*, 1973, 248(10):3660-3669.

Allen and Majerus, "Isolation of vitamin B12-binding proteins using affinity chromatography. I. Preparation and properties of vitamin B12-sepharose," *J. Biol. Chem.*, 1972, 247(23):7695-7701.

Alvarez et al., "On a New Radiopharmaceutical for Kidney Imaging," *Int. J. Appl. Radiat. Isot.*, 1974, 25(6):283-284.

Amagasaki et al., "Expression of Transcobalamin II Receptors by Human Leukemia K562 and HL-60 Cells," *Blood*, 1990, 76(7):1380-1386.

Anderson et al., "Preparation, biodistribution and dosimetry of copper-64-labeled anti-colorectal carcinoma monoclonal antibody fragments 1A3-F(ab')2," *J. Nucl. Med.*, 1995, 36(5):850-858.

Anton et al., "Carbon-13 Nuclear Magnetic Resonance Studies of the Monocarboxylic Acids of Cyanocobalamin. Assignments of the B-, D-, and E-Monocarboxylic Acids," *J. Am. Chem. Soc.*, 1980, 102(7):2215-2219.

Anton et al., "The Synthesis and Properties of Four Spin-Labeled Analogs of Adenosylcobalamin," *J. Biol. Chem.*, 1980, 255:4507-4510.

Armitage et al., "Chemistry of the Vitamin $B_{12}$ Group. Part III. The Course of Hydrolytic Degradations," *J. Chem. Soc.*, 1953, 3849-3861.

Begley et al., "Cobalamin metabolism in cultured human chorionic villus cells," *J. Cell. Physiol.*, 1993, 156:43-47.

Bernhauer et al., "Zur Chemie und Biochemie der Corrinoide," *Biochem. Z.*, 1966, 344:289-309.

Blomquist et al., "Uptake of labeled vitamin B12 and 4-iodophenylalanine in some tumours of mice," *Experientia*, 1969, 25:294-296.

Chaiet et al., "Biosynthesis of radioactive vitamin B12 containing cobalt 60," *Science*, 1950, 111:601-602.

Coderre et al., "Boron Neutron Capture Therapy of a Murine Melanoma," *Cancer Research*, 1988, 48:6313-6316.

Collins et al., "Tumor Imaging via Indium 111-Labeled DTPA-Adenosylcobalamin," *Mayo Clin. Proc.*, 1999, 74:687-691.

Collins et al., "Transcobalamin II Receptor Imaging via Radiolabeled Diethylene-Triaminepentaacetate Cobalamin Analogs," *J. Nucl. Med.*, 1997, 38(5):717-723.

Cooper et al., "Selective Uptake of Specifically Bound Cobalt-58 Bound Cobalt-58 Vitamin B12 by Human and Mouse Tumour Cells," *Nature*, 1961, 191:393-395.

Cooperman, "Distribution of Radioactive and Nonradioactive Vitamin B12 in Normal and Malignant Tissues of an Infant with Neuroblastoma," *Cancer Research*, 1972, 32:167-172.

Cooperman et al., "Distribution of Radioactive and Nonradioactive Vitamin B12 in the Dog," *J. Biol. Chem.*, 1960, 235:191-194.

Ellenbogen, "Absorption and Transport of Cobalamin: Intrinsic Factor and the Transcobalamins," *Cobalamin: Biochem. and Pathophysiol.*, 1975, Babior (ed.), Wiley and Sons, New York, Chapter 5.

Fedosov et al., "Binding of Cobalamin and Cobinamide to Transcobalamin from Bovine Milk," *Biochem.*, 1995, 34:16082-16087.

Fedosov et al., "Transcobalamin from cow milk: isolation and physico-chemical properties," *Biochim. Biophys. Acta*, 1996, 1292:113-119.

Finkler et al., "Nature of the Relationship between Vitamin B12 Binding and Cell Uptake," *Arch. Biochem. Biophys.*, 1967, 120:79-85.

Flodh, "Accumulation of labeled vitamin B12 in some transplanted tumours," *Distribution and Kinetics of Labelled Vitamin B12, Acta Radiologia, Supplementum*, 1968, 284:55-60.

Flodh et al., "Accumulation of labeled vitamin B12 in some transplanted tumours," *Int. J. Cancer*, 1968, 3:694-699.

Ghose et al., "Immunoradioactive Agent against Cancer," *Br. Med. J.*, 1967, 1:90-93.

Ghose et al., "Antibody as Carrier of Chlorambucil," *Cancer*, 1972, 29:1398-1400.

Lau et al., "Measurement of Serum Vitamin B12 Level Using Radioisotope Dilution And Coated Charcoal," *Blood*, 1965, 26(2):202-214.

Grossowicz et al., "Isotopic determination of vitamin B12 binding capacity and concentration," *Proc. Soc. Exp. Biol. Med.*, 1962, 109:604-608.

Hall et al., "Cyclic Activity of the Receptors of Cobalamin Bound to Transcobalamin II," *J. Cell. Physiol.*, 1987, 133:187-191.

Hall et al., "Boron Betaine Analogs: Antitumor Activity and Effects on Ehrlich Ascites Tumor Cell Metabolism," *J. Pharm. Sci.*, 1979, 68(6):685-688.

Hatanaka, "A Revised Boron-Neutron Capture Therapy for Malignant Brain Tumors," *J. Neurol.*, 1975, 209:81-94.

Hatanaka et al., "Clinical Experience of Boron-Neutron Capture Therapy for Gliomas—A Comparison with Conventional Chemo- Immuno-Radiotherapy," *Boron Neutron Capture Therapy for Tumors*, 1986, Chapter 25, pp. 349-378.

Hawthorne et al., "Preparation of Tumor-Specific Boron Compounds. 1. In Vitro Studies Using Boron-Labeled Antibodies and Elemental Boron as Neutron Targets," *J. Med. Chem.*, 1972, 15(5):449-452.

Higashi et al., "In vitro assessment of 2-fluoro-2-deoxy-D-glucose, L-methionine and thymidine as agents to monitor the early response of a human adenocarcinoma cell line to radiotherapy," *J. Nucl. Med.*, 1993, 34:773-779.

Hogenkamp et al., "Diagnostic and Therapeutic Analogues of Cobalamin," *Chemistry and Biochemistry of $B_{12}$*, 1999, R. Banerjee (ed.), John Wiley & Sons, New York, Part II, Section 15, pp. 385-410.

Hogenkamp et al., "Synthesis and Characterization of *nido*-Carborane-Cobalami Conjugates," *Nucl. Med. Biol.*, 2000, 27:89-92.

Hogenkamp et al., "Carbon-13 Nuclear Magnetic Resonance Studies of Adenosylcobalamin and Alkylcorrinoids, Selectivity Enriched with Carbon-13," *Biochemistry*, 1975, 14(16):3707-3714.

Ichihashi et al., "Specific Killing Effect on $^{10}B_1$-Paraboronophenylalanine in Thermal Neutron Capture Theory of Malignant Melanoma: In Vitro Radiobiological Evaluation," *J. Invest. Dermatol.*, 1982, 78(3):215-218.

Jacobsen et al., "Rapid Purification of Cobalamin-Binding Proteins Using Immobilized Aminopropylcobalamin," *Anal. Biochem.*, 1981, 113:164-171.

Kahl et al, "Chemical and Biological Studies on Boronated Tetraphenyl Porphyrins," *Neutron Capture Therapy*, 1986, pp. 61-67.

Kahl et al., "New tumor localizers: Advances in the use of low density lipoproteins (LDL)," *Strahlenther. Onkol.*, 1989, 165:137-139.

Kaplan et al., "Absorptions studies of 59Fe and 58Co vitamin B12 by whole-body radiometry in the radiation therapy of collum carcinoma," *Radiobiol. Radiother.*, 1983, 24, Abstract No. 745.

Kikugawa et al., "Direct halogenation of sugar moiety of nucleosides," *Tetrahedron Letters*, 1971, 2:87-97.

Kubota et al., "Tracer feasibility for monitoring tumor radiotherapy: a quadruple tracer study with fluorine-18-fluorodeoxyglucose or fluorine-18-fluorodeoxyuridine, L-[methyl-14C]methionine, [6-3H]thymidine, and gallium-67," *J. Nucl. Med.*, 1991, 32:2118-2123.

Laster et al., "Dihydroxyboryldeoxyuridine (DBDU); Can a borated nucleoside decide the DNA molecule," *Neutron Capture Therapy*, 1986, pp. 46-54.

Laster et al., "Biological efficacy of a boronated porphyrin as measured in cell culture," *Strahlenther. Onkol.*, 1989, 165:203-205.

Lindemans et al., "Uptake of transcobalamin II-bound cobalamin by HL_60 cells: effect of differentiation induction," *Exp. Cell Res.*, 1989, 184:449-460.

Louisiana State University Cancer Treatment Center, "Chemotherapeutic Agents Commonly used in Veterinary Medicine", http://www.vetmed.lsu.edu/oncology/Chemotherapy.htm, accessed Nov. 14, 2000.

Masiakowski et al., "Gadolinium neutron capture therapy for brain tumors: A computer study," *Med. Phys.*, 1992, 19(5):1277-1284.

McBride, "A general method for the introduction of metal binding ligands onto the side chains of peptides during peptide synthesis," Proc. of the 45th Annual Meeting of the Society of Nuclear Medicine (Los Angeles, California, Jun. 6-10, 1999), *J. Nucl. Med.*, 40(5):124P, Abstract No. 500.

McLean et al., "Antibodies to Transcobalamin II Block In Vitro Proliferation of Leukemic Cells," *Blood*, 1997, 89:235-242.

Mease et al., "Indium-111 CDTA-(aminostyryl)pyridiniumum (di-X-asp) dyes: synthesis, canine and human leukocyte labeling, and serum stability," Proc. of the 46th Annual Meeting of the Society of Nuclear Medicine (Los Angeles, California, Jun. 6-10, 1999), *J. Nucl. Med.*, 40(5):318P, Abstract No. 1396.

Mishima et al., "Prerequisites of First Clinical Trial for Melanoma Selective Thermal Neutron Capture Therapy," *Neutron Capture Therapy*, 1986, pp. 230-236.

Mishima et al., "Treatment of Malignant Melanoma by Single Thermal Neutron Capture Therapy with Melanoma-Seeking $^{10}$B-Compound," *The Lancet*, 1989, 2:388-389.

Mishima et al., "First human clinical trial of melanoma neutron capture. Diagnosis and therapy," *Strahlenthe. Onkol.*, 1989, 165:251-254.

Momen et al., "Impact of High Resolution Bone Spect Imaging of the Thoracolumbar Spine on Patient Management in Oncology," Proc. of the 46th Annual Meeting of the Society of Nuclear Medicine (Los Angeles, California, Jun. 6-10, 1999), *J. Nucl. Med.*, 40(5):102P, Abstract No. 413.

Nakagawa et al., "Syntheses of Chlorpromazine Undecahydrododecaborate and Nonahydrodecaborate-Promising Agents for Neutron Capture Therapy of Malignant Melanoma," *Chem. Pharm. Bull.*, 1976, 24(4):778-781.

Nexø, "Cobalamin Binding Proteins," *Vitamin B12 and B12-proteins*, 1997, Krantler et al. (eds.), Wiley & Sons, New York, Chapter 30, pp. 461-475.

Norenberg et al., "[$^{213}$BI-DOTA$^0$,TYR$^3$]Octreotide ($^{213}$BI-Dotatoc) in Peptide Receptor Radionuclide Therapy (PRRT)," Proc. of the 46th Annual Meeting of the Society of Nuclear Medicine (Los Angeles, California, Jun. 6-10, 1999), *J. Nucl. Med.*, 40(5):103P, Abstract No. 415.

Order et al., "Use of Isotopic Immunoglobulin in Therapy," *Cancer Res.*, 1980, 40:3001-3007.

Pisal et al., "Formulation of nasal gels of Vitamin B12-1: Effect of additives on thermodynamic properties of pluronic PF-127 gels," *Indian J. Pharm. Sci.*, 2002.

Ponto, "II. Schilling Test," *Pharmaceutical in Medical Imaging*, Swanson et al. (eds.), MacMillan Publishing Co., Inc., New York, NY, 1990, pp. 621-628.

Primus et al., "Bispecific Antibody Mediated Targeting of *nido*-Carboranes to Human Colon Carcinoma Cells," *Bioconjugate Chem.*, 1996, 7:532-535.

Rao et al., "TC-99M Labeled Peptide for Imaging Infection," Proc. of the 46th Annual Meeting of the Society of Nuclear Medicine (Los Angeles, California, Jun. 6-10, 1999), *J. Nucl. Med.*, 40(5):319P, Abstract No. 1398.

Rappazzo and Hall, "Transport Function of Transcobalamin II," *J. Clin. Invest.*, 1972, 51:1915-1918.

Roe et al., "Combinatorially Designed Technetium Radiopharmaceuticals (CDTR™)," Proc. of the 46th Annual Meeting of the Society of Nuclear Medicine (Los Angeles, California, Jun. 6-10, 1999), *J. Nucl. Med.*, 40(5):123P, Abstract No. 499.

Ruiz et al., "Influence of average molecular weights of poly(DL-lactic acid-co-glycolic acid) copolymers 50/50 on phase separation and in vitro drug release from microspheres," *Pharm. Res.*, 1990, 7(9):928-934.

Sattelberger and Atcher, "Nuclear medicine finds the right chemistry," *Nat. Biotechnol.*, 1999, 17:849-850.

Schinazi et al., "Synthesis and Properties of Boron and Silicon Substituted Uracil or 2'-Deoxyuridine," *Tetrahedron Letters*, 1978, 50:4981-4984.

Shih and Brugger, "Gadolinium as a neutron capture therapy agent," *Med. Phys.*, 1992, 19:733-744.

Smeltzer et al., "Synthesis and Characterization of Fluorescent Cobalamin (CobalaFluor) Derivatives for Imaging," *Org. Lett.*, 2001, 3(6):799-801.

Sneath et al., "Protein-Binding Polyhedral Boranes," *J. Med. Chem.*, 1976, 19(11):1290-1294.

Soda et al., "Receptor and Distribution and the Endothelial Uptake of Transcobalamin II in Liver Cell Suspensions," *Blood*, 1985, 65(4):795-802.

Svanvik et al., "Light-up probes: thiazole orange-conjugated peptide nucleic acid for detection of target nucleic acid in homogeneous solution," *Analyt. Biochem.*, 2000, 281:26-35.

Toraya et al., "Preparation, Properties and Biological Activities of Succinyl Derivatives of Vitamin $B_{12}$," *Bioinorg. Chem.*, 1975, 4:245-255.

Uchino et al., "Tissue Distribution of Coenzyme B12 in Rats Following Intravenous Administration," *Ann. N.Y. Acad. Sci.*, 1964, 112:844-854.

van Eijkeren et al., "Measurement of short-term 11C-thymidine activity in human head and neck tumours using positron emission topography (PET)," *Acta Oncol.*, 1992, 31(5):539-543.

Vares and Myasishcheva, "Kinetic of $^{57}$Co-cyanocobalamin distribution in organs and tissues of mice with transplanted tumours," *Eksp. Onkol.*, 1986, 8:33-36, English Abstract.

Wierzbicki et al., "Measurement of augmentation of $^{252}$Cf implant by $^{10}$B and $^{157}$Gd neutron capture," *Med. Phys.*, 1994, 21(6):787-790.

Wilbur et al., "Biotin Reagents for Antibody Pretargeting. 4. Selection of Biotin Conjugates for in Vivo Application Based on Their Dissociation Rate from Avidin and Streptavidin," *Bioconj. Chem.*, 2000, 11(4):569-583.

Wilbur et al., "Evaluation of Biotin-Dye Conjugates for Use in an HPLC Assay to Assess Relative Binding of Biotin Derivatives with Avidin and Streptavidin," *Bioconj. Chem.*, 2000, 11(4):584-598.

Woolley et al., "Uptake of [Co-57]-vitamin B-12 by murine tumours of many histological types," *Clin. Res.*, 1993, 41:73A, Abstract.

Wu et al., "Investigation of N-linked Macrocytes for $^{111}$In and $^{90}$Y Labeling of Proteins," *Nucl. Med. Biol.*, 1992, 19(2):239-244.

Yamada and Hogenkamp, "The synthesis of a 5'-deoxyadenosylcobalamin-agarose adsorbent and its utility in the purification of ribonucleotide reductase," *J. Biol. Chem.*, 1972, 247(19):6266-6270.

Good et al., "Antisense inhibition of gene expression in bacteria by PNA targeted to mRNA," *Nat. Biotechnol.*, 1998, 16(4):355-358.

Pinson et al., "Synthesis, Protein Binding, and Cellular Uptake of Doxorubicin-Cobalamin Bioconjugates," *Am. Chem. Soc.*, Abstracts of National Meeting, 2000, vol. 219, Abstract No. 82.

Whittacker, "Biosynthesis of a Thiouracil Pheomelanin in Embryonic Pigment Cells Exposed to Thiouracil," *J. Biol. Chem.*, 1971, 246(20):6217-6226.

\* cited by examiner

RADIONUCLIDE LABELING OF VITAMIN $B_{12}$ AND COENZYMES THEREOF

CROSS-REFERENCE TO RELATED APPLICATIONS

This application is a continuation application of U.S. application Ser. No. 10/620,273, filed on Jul. 15, 2003, now U.S. Pat. No. 7,141,233, which is a divisional of U.S. patent application Ser. No. 09/626,213, filed Jul. 26, 2000, now U.S. Pat. No. 6,613,305, which is a divisional of U.S. application Ser. No. 09/354,553, filed Jul. 15, 1999, now U.S. Pat. No. 6,096,290, which is a divisional of U.S. application Ser. No. 09/059,277, filed Apr. 13, 1998, now U.S. Pat. No. 6,004,533, which is a divisional of U.S. application Ser. No. 08/557,955, filed Nov. 13, 1995, now U.S. Pat. No. 5,739,313, and related to U.S. patent application Ser. No. 09/500,780, filed Feb. 8, 2000, now U.S. Pat. No. 6,211,355, all of which are incorporated by reference in their entirety herein.

BACKGROUND OF THE INVENTION

For several years after the isolation of vitamin $B_{12}$ as cyanocobalamin in 1948, it was assumed that cyanocobalamin and possibly hydroxocobalamin, its photolytic breakdown product, occurred in man. Since then it has been recognized that cyanocobalamin is an artifact of the isolation of vitamin $B_{12}$ and that hydroxocobalamin and the two coenzyme forms, methylcobalamin and adenosylcobalamin, are the naturally occurring forms of the vitamin.

The structure of these various forms is shown in FIG. 1, wherein X is CN, OH, $CH_3$ or adenosyl, respectively. Hereinafter, the term cobalamin will be used to refer to all of the molecule except the X group. The fundamental ring system without cobalt (Co) or side chains is called corrin and the octadehydrocorrin is called corrole. The Co-contg heptacarboxylic acid resulting from hydrolysis of all the amide groups without the CN and the nucleotide, is designated cobyrinic acid. The corresponding hexacarboxylic acid with D-1-amino-2-propanol side chain f is called cobinic acid and the hexacarboxylic acid with the α-D-ribofuranose-3-phosphate attached to the 2-position of the amino propanol is called cobamic acid. Thus, cobamide is the hexaamide of cobamic acid, cobyric acid is the hexaamide of cobyrinic acid and cobinamide is the hexaamide of cobinic acid. FIG. 1 is adapted from *The Merck Index*, Merck & Co. (11th ed. 1989), wherein X is above the plane defined by the corrin ring and nucleotide is below the plane of the ring. The corrin ring has attached six amidoalkyl ($H_2NC(O)Alk$) substituents, at the 2, 3, 7, 8, 13, and 18 positions, which can be designated a-e and g, respectively. See D. L. Anton et al., *J. Amer. Chem. Soc.*, 102, 2215 (1980). The molecule shown in FIG. 1 can be abbreviated as shown below:

wherein, e.g., X is CN, OH, $CH_3$, or adenosyl.

Methylcobalamin serves as the cytoplasmic coenzyme for $^5$N-methyltetrahydrofolate:homocysteine methyl transferase (methionine synthetase, EC 2.1.1.13), which catalyzes the formation of methionine from homocysteine. Adenosylcobalamin is the mitochondrial coenzyme for methylmalonyl CoA mutase (EC5.4.99.2) which interconverts methylmalonyl CoA and succinyl CoA.

All forms of vitamin $B_{12}$ (adenosyl-, cyano-, hydroxo-, or methylcobalamin) must be bound by the transport proteins, Intrinsic Factor and Transcobalamin II to be biologically active. Specifically, gastrointestinal absorption of vitamin $B_{12}$ relies upon the intrinsic factor-vitamin $B_{12}$ complex being bound by the intrinsic factor receptors in the terminal ileum. Likewise, intravascular transport and subsequent cellular uptake of vitamin $B_{12}$ throughout the body is dependent upon transcobalamin II and the cell membrane transcobalamin II receptors, respectively. After the transcobalamin II-vitamin $B_{12}$ complex has been internalized, the transport protein undergoes lysozymal degradation, which releases vitamin $B_{12}$ into the cytoplasm. All forms of vitamin $B_{12}$ can then be interconverted into adenosyl-, hydroxo-, or methylcobalamin depending upon cellular demand. See, for example, A. E. Finkler et al., *Arch. Biochem. Biophys.*, 120, 79 (1967); C. Hall et al., *J. Cell Physiol.*, 133, 187 (1987); M. E. Rappazzo et al., *J. Clin. Invest.*, 51, 1915 (1972) and R. Soda et al., *Blood*, 65, 795 (1985).

Cells undergoing rapid proliferation have been shown to have increased uptake of thymidine and methionine. (See, for example, M. E. van Eijkeren et al., *Acta Oncologica*, 31, 539 (1992); K. Kobota et al., *J. Nucl. Med.*, 32, 2118 (1991) and K. Higashi et al., *J. Nucl. Med.* 34, 773 (1993)). Since methylcobalamin is directly involved with methionine synthesis and indirectly involved in the synthesis of thymidylate and DNA, it is not surprising that methylcobalamin as well as Cobalt-57-cyanocobalamin have also been shown to have increased uptake in rapidly dividing tissue (for example, see, B. A. Cooper et al., *Nature*, 191, 393 (1961); H. Flodh, *Acta Radiol. Suppl.*, 284, 55 (1968); L. Bloomquist et al., *Experientia*, 25, 294 (1969)). Additionally, upregulation in the number of transcobalamin II receptors has been demonstrated in several malignant cell lines during their accelerated thymidine incorporation and DNA synthesis (see, J. Lindemans et al., *Exp. Cell. Res.*, 184, 449 (1989); T. Amagasaki et al., *Blood*, 26, 138 (1990) and J. A. Begly et al., *J. Cell Physiol.*, 156, 43 (1993).

Vitamin $B_{12}$ has several characteristics which potentially make it an attractive in vivo tumor imaging agent. Vitamin $B_{12}$ is water soluble, has no known toxicity, and in excess is excreted by glomerular filtration. In addition, the uptake of vitamin $B_{12}$ could potentially be manipulated by the administration of nitrous oxide and other pharmacological agents (D. Swanson et al., *Pharmaceuticals in Medical Imaging*, MacMillan Pub. Co., NY (1990) at pages 621-628).

Bacteria naturally insert Cobalt-59 into the corrin ring of vitamin $B_{12}$. Commercially this has been exploited by the fermentative production of Co-56, Co-57, Co-58, and Co-60 radiolabeled vitamin $B_{12}$. For example, see Chaiet et al., *Science*, 111, 601 (1950). Unfortunately Cobalt-57, with a half life of 270.9 days, makes Co-57-cyanocobalamin unsuitable for clinical tumor imaging. Other metal ions (cobalt, copper and zinc) have been chemically inserted into naturally occurring descobaltocorrinoids produced by *Chromatium* and *Streptomyces olivaceous*. Attempts to chemically insert other metal ions in these cobalt free corrinoid rings has been unsuccessful. The placement of metals (cobalt, nickel, palladium, platinum, rhodium, zinc, and lithium) into a synthetic corrin ring has not presented any major difficulties. However, their instability and cost to produce makes them impractical for biological assay-s. Although Co-59 is a weakly paramagnetic quadrapolar nuclei in the $2^+$ oxidation state, Co-59 exists in the $3^+$ oxidation state within the corrin ring of vitamin $B_{12}$ and is diamagnetic. Therefore, insertion of either a radioactive or paramagnetic metal ion other than cobalt into the corrin ring does not seem feasible at this time.

A process for preparing $^{125}$I-vitamin $B_{12}$ derivatives is described in Niswender et al. (U.S. Pat. No. 3,981,863). In this process, vitamin $B_{12}$ is first subjected to mild hydrolysis to form a mixture of monocarboxylic acids, which Houts, infra disclosed to contain mostly the (e)-isomer. The mixture is then reacted with a p-(aminoalkyl)phenol to introduce a phenol group into the $B_{12}$ acids (via reaction with one of the free carboxylic acid groups). The mixed substituent $B_{12}$ derivatives are then iodinated in the phenol-group substituent. This U.S. patent teaches that the mixed $^{125}$I-$B_{12}$ derivatives so made are useful in the radioimmunoassay of $B_{12}$, using antibodies raised against the mixture.

T. M. Houts (U.S. Pat. No. 4,465,775) reported that the components of the radiolabelled mixture of Niswender et al. did not bind with equal affinity to IF. Houts disclosed that radioiodinated derivatives of the pure monocarboxylic (d)-isomer are useful in assays of $B_{12}$ in which IF is used. However, although Houts generally discloses that the monocarboxylic (d)-isomer can be labelled with fluorophores or enzymes and used in competitive assays for vitamin $B_{12}$ in fluids, a continuing need exists for labelled vitamin $B_{12}$ derivatives suitable for tumor and organ imaging and therapy.

SUMMARY OF THE INVENTION

The present invention provides detectable compounds of the general formula (I):

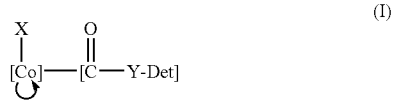

(I)

wherein the moiety

is cobalamin, X is CN, OH, methyl or adenosyl,

is the residue of a monocarboxylic acid of the cobalamin, derived from a corrin propionamide group, and is preferably the essentially pure (b)-, (d)-, or (e)-monocarboxylic acid; Y is a linking group and Det is a chelating group comprising a detectable metal, such as a radionuclide or paramagnetic metal ion. Preferably, the linking group is —N(H)(CH$_2$)$_{2-6}$NH—.

For example, compounds of formula (I) derived from the (b)-monocarboxylic acid, wherein Det is the diethylenetriaminepentaacetic acid group (DTPA), were prepared comprising Tc-99n, In-111 and Gd-153. These compounds were found to be readily absorbed through the mammalian peritoneal membrane and gastrointestinal tract, to localize within the liver, kidney, pancreas, and spleen. Therefore, the present compounds can be used to evaluate hepatic, splenic, renal, pancreatic, and small bowel function in mammals such as humans and experimental animals, by administering a compound of formula (I) to the mammal and detecting its presence in the target organ, using appropriate normal control values for comparison.

Certain neoplastic tissue has been found to act as a vitamin $B_{12}$ sink, accumulating the vitamin to a greater extent than the surrounding slower dividing tissue. Therefore, the present compounds can also be used for tumor imaging and/or targeted cancer therapy, by administering a compound of formula (I) to a mammal afflicted with a tumor, so that the compound localizes in the tumor, and optionally, detecting the presence of the compound in the tumor, particularly tumors of the organs listed above.

Intermediates useful in the preparation of the compounds of formula (I) are also an aspect of the invention, including compounds wherein Det is replaced by Chel, which is an organic chelating group, or chelator, capable of chelating a radionuclide or radioisotope.

DETAILED DESCRIPTION OF THE INVENTION

Figure 1:
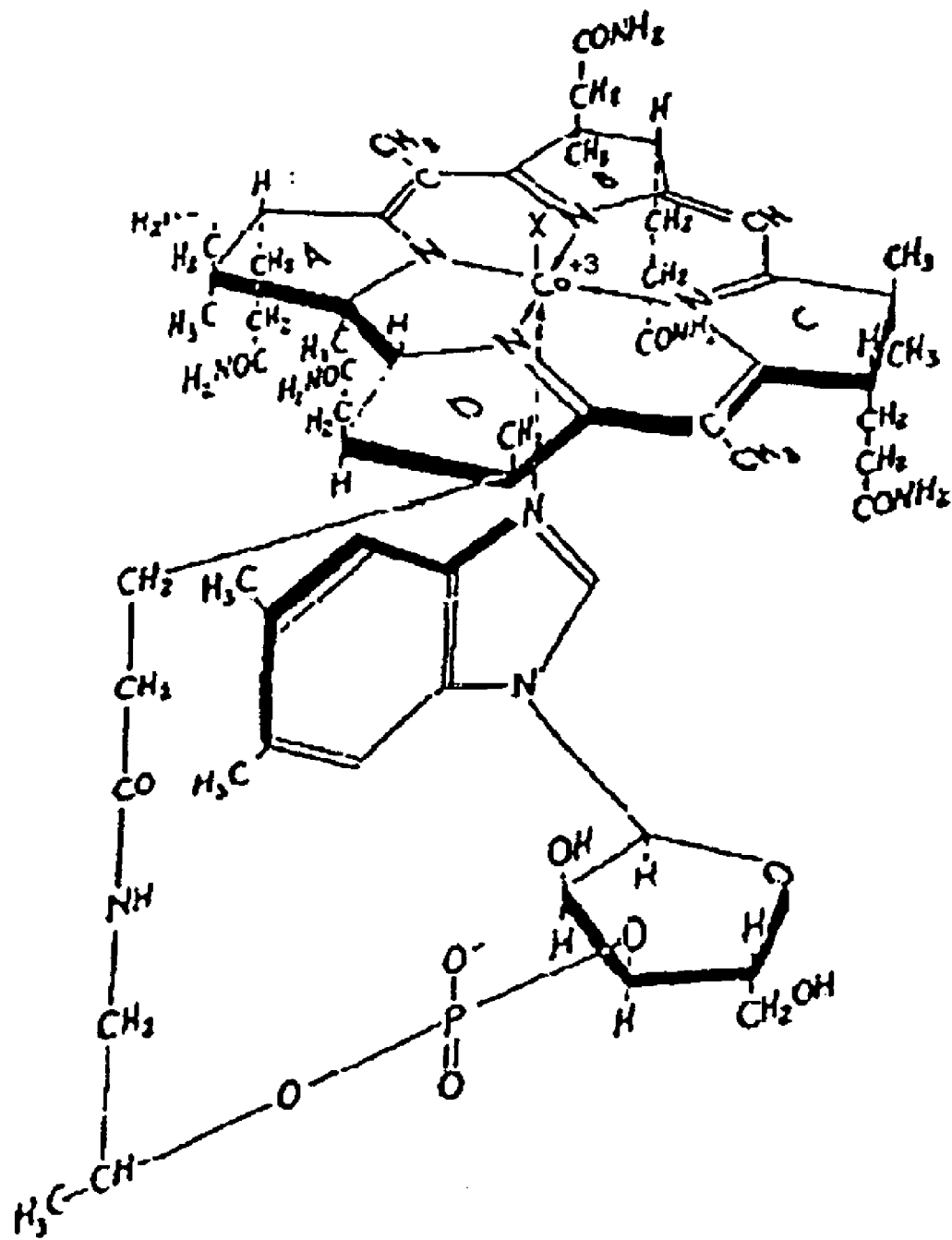
FIG. 1 depicts the structure of vitamin $B_{12}$, wherein X is CN (cyano), OH, CH$_3$ or adenosyl.

The compounds of formula I can be prepared by producing a monocarboxylic acid of X-[cobalamin], wherein X is cyano-, methyl; adenosyl, and the like. These compounds can be prepared by the mild acid hydrolysis of cyanocobalamin, which has been shown to yield a mixture of mono-, a dicarboxylic acids and one tricarboxylic acid. These carboxylic acids are derived from the propionamide side chains designated b, d and e, as discussed hereinabove, which are more susceptible to hydrolysis than the amide groups on acetamide side chains a, c, and g. The (b)-, (d)-, and (e)-monocarboxylic acids can be separated by column chromatography. See FIG. 1 herein, and FIG. 1 of D. L. Anton et al., *J. Amer. Chem. Soc.*, 102, 2215 (1980). See, also, J. B. Armitage et al., *J. Chem. Soc.*, 3349 (1953); K. Bernhauer, *Biochem. Z.*, 344, 289 (1966); H. P. C. Hogenkamp et al., *Biochemistry*, 14, 3707 (1975); and L. Ellenbogen, in "Cobalamin," *Biochem. and Pathophysiol.*, B. Babior, ed., Wiley, N.Y. (1975) at chapter 5.

The X-[cobalamin] [CO$_2$H] can be linked to the metal chelator by means of a linking group, which is preferably a divalent, or "bifunctional" organic linking group. Such linking groups comprise two reactive groups, one that is coupled to the CO$_2$H group, and the other that is coupled to the metal chelator. A variety of homobifunctional and heterobifunctional linking reagents known in the art are useful in the present invention. Preferred linkers comprise one or two amino or hydroxyl groups, such as ω-aminoalkanoic acids, e.g., ε-amino caproic acid (H$_2$N—(CH$_2$)$_5$—COOH), or alkane diamines including 1,4-diaminobutane, 1,5-diaminopentane and 1,6-diaminohexane, and the like. Particularly preferred among the aminoalkanoic acids and similar compounds are those which are soluble in aqueous buffers.

Det is a chelating group comprising a radionuclide, such as a metallic radioisotope. Preferred among these chelating compounds "chelators" or (chel) are such polycarboxylic acids as EDTA, DTPA, DCTA, DOTA, TETA, or analogs or homologs thereof.

DTPA (diethylenetriaminepentaacetic acid) can be attached to cobalamin carboxylic acid(s) via reaction of diethylenetriaminepentaacetic dianhydride (Aldrich Chem. Co.) with a linker comprising a free amino group. This yields a Chel group that is 2-(amidomethyl)-1,1,7,7-diethylenetriaminetetraacetic acid. This chelator can be reacted with radionuclides to yield a Det moiety of the general formula

Figure 2:
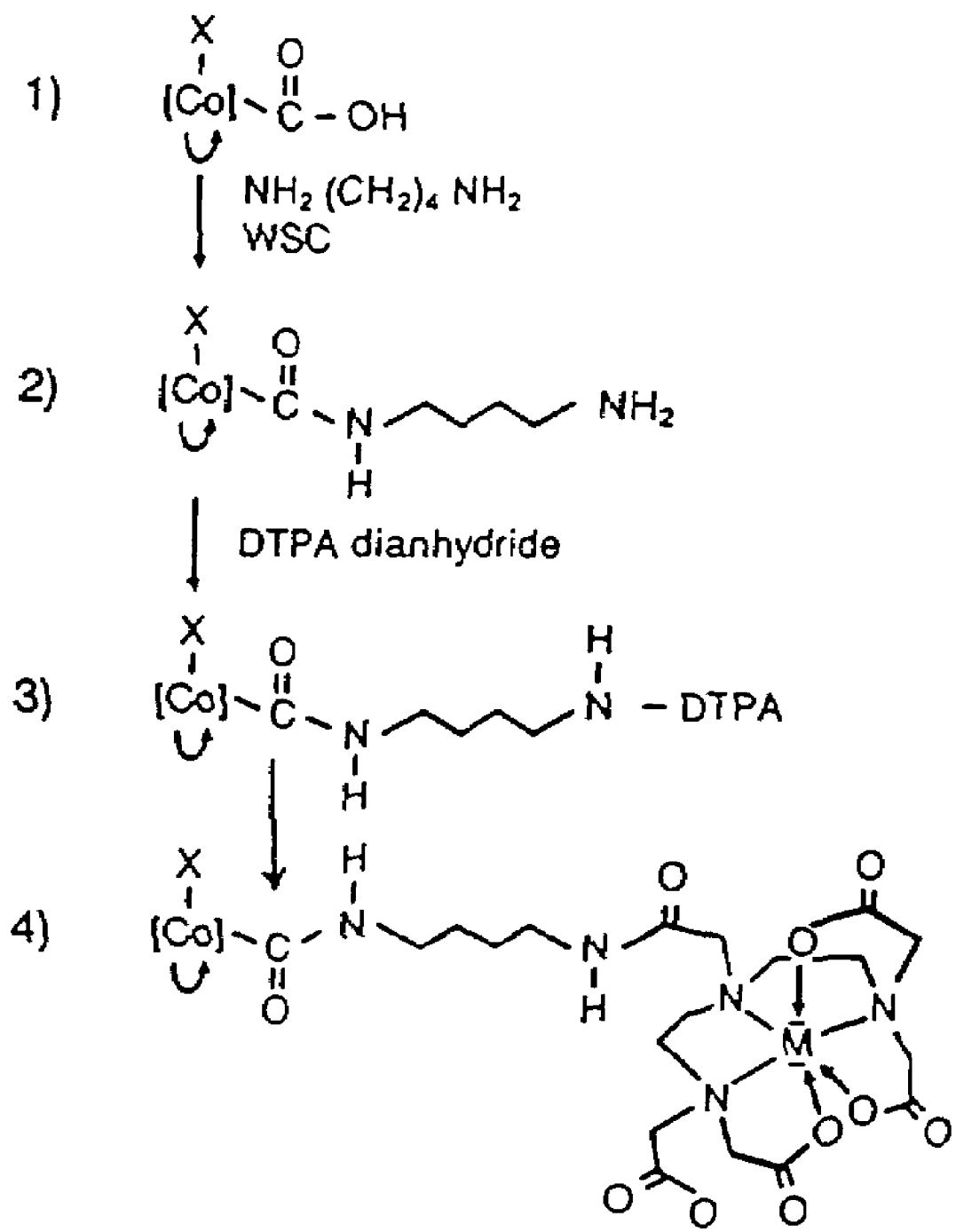
FIG. 2 schematically depicts the synthesis of a cobalamin metal ion DTPA complex.

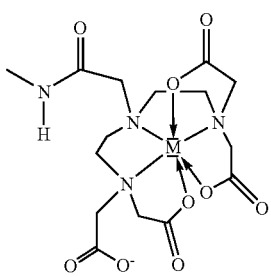

wherein M is the radionuclide. The synthetic route to a cobalamin metal ion DTPA complex (4) is schematically shown in FIG. 2, wherein WSC=water soluble carbodiimide.

The chelator (chel) DCTA has the general formula:

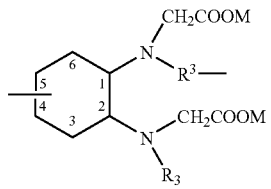

DCTA is a cyclohexane-based metal chelator, wherein $R^3$ may by $(C_1-C_4)$alkyl or $CH_2CO_2$—, which may be attached to the Y through positions 4 or 5, or through the group $R^3$ and which carries from 1 to 4 detectable metal or nonmetal cations (M), monovalent cations, or the alkaline earth metals. Thus, with metals of oxidation state +1, each individual cyclohexane-based molecule may carry up to 4 metal cations (where both $R^3$ groups are $CH_2COOM$). As is more likely, with higher oxidation states, the number of metals will decrease to 2 or even 1 per cyclohexane skeleton. This formula is not intended to limit the molecule to any specific stereochemistry. In particular, both amino functionalities may be either cis or trans to each other.

Other macrocyclic carboxylic acid chelators which can be linked to the cobalamin carboxylic acid via bis-amino linking groups include TETA 1,4,8,11-tetraazacyclotetradecane-N,N',N'',N'''-tetraacetic acid; 1,4,7,10-tetraazacyclododecane-N,N',N'',N'''-tetraacetic acid (DOTA); 1,4,8,12-tetraazacyclopentadecane-N,N',N'',N'''-tetraacetic acid (15N4); 1,4,7-triazacyclononane-N,N',N''-triacetic acid (9N3); and 1,5,9-triazacyclododecane-N,N',N''-triacetic acid (12N3). Bifunctional chelators based on macrocyclic ligands in which conjugation is via an activated arm attached to the carbon backbone of the ligand can be employed as described by M. Moi et al., *J. Amer. Chem. Soc.*, 49, 2639 (1989) (2-p-nitrobenzyl-1,4,7,10-tetraazacyclododecane-N,N',N'',N'''-tetraacetic acid); S. V. Deshpande et al., *J. Nucl. Med.*, 31, 473 (1990); G. Ruser et al., *Bioconj. Chem.*, 1, 345 (1990); C. J. Broan et al., *J. C. S. Chem. Comm.*, 23, 1739 (1990); and C. J. Anderson et al., *J. Nucl. Med.*, 36, 850 (1995) (6-bromoacetamido-benzyl-1,4,8,11-tetraazacyclotetradecane-N,N',N'',N'''-tetraacetic acid (BAT)).

Any metal capable of being detected in a diagnostic procedure in vivo or in vitro can be employed as M in the Det moieties. Particularly, any radioactive metal ion capable of producing a diagnostic result in a human or animal body or in an in vitro diagnostic assay may be used in the practice of the present invention. Suitable ions include the following: Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-56, Cobalt-57, Cobalt-58, Cobalt-60, Cobalt-64, Erbium-169, Europium-152, Gadolinium-153, Gold-195, Gold-199, Hafnium-175, Hafnium-175-181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-7147, Protactinium-233, Radium-226, Rhenium-186, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Titanium-44, Tungsten-1.85, Vanadium-48, Vanadium-49, Ytterbium-169, Yttrium-88, Yttrium-90, Yttrium-91, Zinc-65, and Zirconium-95.

The compounds of formula (I) are preferable dissolved or dispersed in a nontoxic liquid vehicle, such as physiological saline or a similar aqueous vehicle, to the desired concentration. A preselected analytical, diagnostic or therapeutic unit dose is then administered to the test animal or human patient, by oral administration or ingestion or by parenteral administration, as by intravenous or intraperitoneal infusion or injection, to attain the desired in vivo concentration. Doses useful for imaging or treating human organs or tumors can be derived, from those found to be effective to image or treat organs in humans in vitro or in animal models, such as those described hereinbelow, or from dosages of other labelled vitamin $B_{12}$ molecules, previously employed in animal therapy or imaging.

The invention will be further described by reference to the following detailed examples, wherein cyanocobalamin and 1-ethyl-3-(3-dimethylaminopropyl) carbodiimide were purchased from Sigma Chem. Co., St. Louis, Mo. Adenosine, 1,4-diaminobutane dihydrochloride, diethylenetriamine pentaacetic (DPTA), hexamethylphosphoramide, 1-hydroxybenzotriazole hydrate, iodomethane and thionylchloride were obtained from Aldrich Chem. Co., Milwaukee, Wis. Thin layer chromatography (TLC) silica gel and PET-cellulose sheets were purchased from E. M. Science, Gibbstown, N.J. $Tc^{99m}$ and $In^{111}$ were obtained from Mallinckrodt Medical, Inc. and $Gd^{153}$ was obtained from Amersham. Other inorganic salts and solvents were obtained in the highest purity available.

UV-visible spectra were recorded on a Hewlett-Packard diode array spectrophotometer. DTPA dianhydride and 5'-chloro-5'-deoxyadenosine were synthesized as described by W. C. Eckelman et al., *J. Pharm. Sci.*, 64, 704 (1975) and K. Kikugawa et al., *Tetrahedron Lett.*, 87 (1971), respectively. The monocarboxylic acids of cyanocobalamin, methylcobalamin-b-carboxylic acid and adenosylcobalamin-b-carboxylic acid were prepared and isolated as described by H. P. C. Hogenkamp, *Biochemistry*, 13, 2736 (1974); D. L. Anton et al., *J. Amer. Chem. Soc.*, 102, 2215 (1980); R. H. Yamada et al., *J. Biol. Chem.*, 247, 6266 (1972) and D. Dolphin, *Methods in Enzymology*, XVille, 34-52 (1971). Methylcobalamin, adenosylcobalamin and their derivatives are light sensitive, especially in solution, and all reactions and manipulations were carried out in the dark or in dim light.

All images for the in vivo studies were obtained on a GE 500 maxicamera using a LEAP collimator with a 20% window about the 140 keV energy peak of technetium, and a medium energy collimator with a 20% window about the 174 keV and 247 keV energy peaks of Indium. A 256×256 matrix with a dedicated pinnacle computer system was used to collect and analyze the data.

EXAMPLE 1

Cyanocobalamin-b-(4-aminobutyl)amide

A mixture containing cyanocobalamin-b-carboxylic acid (1.0 g, 0.6 mmol), hydroxybenzotriazole (0.81 g, 6 mmol)

and 1,4-diaminobutane dihydrochloride (4.8 g, 30 mmol) in 100 ml of water was adjusted to pH 7.8. 1-Ethyl-3-(3'-dimethylaminopropyl)carbodiimide (1.26 g, 6.6 mmol) was then added, the pH was adjusted to 6.4 and the reaction stirred at room temperature for 24 h. TLC on silica gel using n-butanol-acetic acid water (5:2:3) showed the reaction to be complete. Cyanocobalamin-b-(4-aminobutyl)amide was extracted into 92% aqueous phenol and the phenol layer was washed several times with equal volumes of water. To the phenol extract were added 3 volumes of diethylether and 1 volume of acetone. The desired cobalamin was removed from the organic phase by several extractions with water. The combined aqueous layers were extracted three times with diethylether to remove residual phenol, concentrated to approximately 20 ml in vacuo and crystallized from aqueous acetone. Yield 955 mg, 92%.

EXAMPLE 2

Cyanocobalamin-b-(4-aminobutyl)amide DTPA

Cyanocobalamin-b-(4-aminobutyl) amide (500 mg), 0.3 mmol) was dissolved in 30 ml sat. sodium bicarbonate and treated with solid DTPA dianhydride (1.2 g, 3.4 mmol). The progress of the reaction was monitored by TLC on PEI plates using n-butanol-acetic acid-water (5:2:3) as the solvent. After 30 min incubation at room temperature a second 1.2 g of the dianhydride was added. After two additional additions of dianhydride with adjustments of the pH to 8.2 the reaction mixture was incubated overnight. Cyanocobalamin-DPTA adduct was then extracted into 92% aqueous phenol and purified as described above. The preparation was evaporated to dryness in vacuo and isolated as a glass. Yield 460 mg, 77%. The cyanobalamin-DTPA adduct behaves as a polyanion on paper electrophoresis in 0.1 M sodium phosphate buffer pH 7.1.

EXAMPLE 3

Methylcobalamin-b-(4-aminobutyl)amide

Methylcobalamin-b-carboxylic acid (1.0 g, 0.6 mmol) was reacted with diaminobutane dihydrochloride as described above for the cyano derivative. The cobalamin was purified by extraction through phenol (see above) and the resulting aqueous solution was concentrated in vacuo. This solution was chromatographed on AG1-X2 200-400 mesh in the acetate form (20×2.5 cm) and the pass through collected. The pass through was concentrated to approximately 20 ml and the desired cobalamin crystallized from aqueous acetone. Yield 920 mg, 88%. Unreacted methylcobalamin-b-carboxyclic acid was eluted with 1 M acetic acid, concentrated and crystallized from aqueous acetone. Yield 60 mg, 6%.

EXAMPLE 4

Methylcobalamin-b-(4-aminobutyl)amide DTPA

Methylcobalamin-b-(4-aminobutyl)amide (500 mg, 0.3 mmol) was dissolved in 30 ml saturated sodium bicarbonate and reacted with solid DTPA dianhydride as described above. The methyl cobalamin-DTPA adduct was purified by extraction through phenol, evaporated to dryness in vacuo and isolated as a glass. Yield 600 mg, 96%.

EXAMPLE 5

Adenosylcobalamin-b-(4-aminobutyl)amide

Adenosylcobalamin-b-carboxylic acid (500 mg, 0.3 mmol) was reacted with diaminobutane dihydrochloride (2.4 mg, 15 mmol) as described above. The cobalamin was purified by extraction through phenol (see above). The resulting aqueous solution was concentrated in vacuo and applied to AG-50 X2, 200-400 mesh, in the hydrogen form (20×25 cm). The column was washed thoroughly with water to remove hydroxybenzotriazole and the desired cobalamin eluted with 1 M ammonium hydroxide. After an additional extraction through phenol, adenosylcobalamin-b-(4-aminobutyl)amide was isolated as a glass. Yield 366 mg, 77%.

EXAMPLE 6

Adenosylcobalamin-b-(4-aminobutyl)amide DTPA

Adenosylcobalamin-b-(4-aminobutyl)amide (366 mg. 0.23 mmol) was dissolved in 30 ml saturated sodium bicarbonate and treated with solid DTPA dianhydride (1.0 g, 2.8 mmol) as described above. The cobalamin was purified through phenol (see above). The resulting aqueous solution was concentrated and applied to AG-50×2, 200-400 mesh, in the hydrogen form (6.0×2.5 cm), the column was washed with water and the desired cobalamin eluted with 0.1 M ammonium hydroxide. The solution was evaporated to dryness in vacuo and adenosylcobalamin-b-(4-aminobutyl) amide DTPA isolated as a glass. Yield 400 mg, 80%.

EXAMPLE 7

Interaction with Intrinsic Factor and Transcobalamin Proteins

Under dim light, 1000 µg of the non-labeled methyl-, adenosyl-, and cyanocobalamin-b-(4-aminobutyl)amide-DTPA, as well as 1000 µg of cyanocobalamin and DTPA (Sigma, St. Louis, Mo. 63178), were separately dissolved in 10 ml of normal saline at room temperature. Each of the five 1000 µg/10 ml samples were stored in sealed, aluminum-Tapped 10 ml vials to prevent exposure to light. No buffers were added to the solutions. The pH of the solutions, measured by a Beckman 40 pH meter (Beckman Instruments, Fullerton, Calif.): Cyanocobalamin=5.75, DTPA=3.78; cyano, methyl and adenosylcobalamin-DTPA analogues were 5.75, 6.10, and 6.19, respectively.

To assess in vitro binding to Intrinsic Factor (IF) and Transcobalamins (TC), the intrinsic factor blocking antibody (IFBA) and Unsaturated vitamin $B_{12}$ Binding Capacity (UBBC) assays were performed with serum randomly obtained from five patients being evaluated for pernicious anemia at the Mayo Clinic. The IFBA and UBBC assays were first performed for clinical purposes as previously described by V. F. Fairbanks et al., *Mayo Clin. Proc.,* 58, 203 (1983); Intrinsic Factor Blocking Antibody [$^{57}$Co] Radioassay-Package insert, Diagnostic Products Corp.; D. Grossowicz et al., *Proc. Exp. Biol.* 109, 604 (1962) and C. Gottlieb et al., *Blood* 25, 6 (1965).

Next, the serum from the same five patients underwent modified IFBA and UBBC assays. Specifically, 1 µl of the five previously described solutions were separately incubated with purified IF or serum, to potentially saturate all IF and TC binding sites. After incubation for 20 minutes at room temperature and for another 20 minutes at 4° C., 500 µl of the stock (1000 µg/l) Cobalt-57-cyanocobalamin (Mallinckrodt Medical. Inc., St. Louis, Mo. 63134) solution was added and the usual IFBA and UBBC protocols were then followed. All supernatant activity was counted for four minutes on a gamma counter (Micromedix 10/20, Huntsville, Ala. 35805). The results are shown in Table I.

TABLE I

| Clinical Run | CNB$_{12}$ | MEB$_{12}$DTPA | ADB$_{12}$DTPA | CNB$_{12}$DTPA | DTPA |
|---|---|---|---|---|---|
| UBBC | | | | | |
| PT 1 | 741 | <NSB | 17.1 | 54.6 | 222.6 | 731.5 |
| PT 2 | 632 | <NSB | 26.8 | 62.6 | 216.9 | 913.1 |
| PT 3 | 2097 | <NSB | 278.9 | 590.3 | 713.3 | 2078.9 |
| PT 4 | 1378 | <NSB | 60.9 | 126.9 | 433.2 | 1633.7 |
| PT 5 | 1682 | <NSB | 91.1 | 163.9 | 643.2 | 1418.0 |
| IFBA | | | | | |
| PT 1 | 11942.5 | 951.5 | 4279 | 6758.5 | 5151 | 11899 |
| | (0.99) | (12.48) | (2.77) | (2.30) | (2.30) | (0.99) |
| PT 2 | 11656 | 920.5 | 4082 | 6841.5 | 5133.5 | 11696.5 |
| | (1.02) | (12.90) | (2.92) | (1.74) | (2.31) | (1.02) |
| PT 3 | 11780 | 912.5 | 4456.5 | 6828.5 | 5338.5 | 11735.5 |
| | (1.01) | (13.01) | (2.66) | (1.74) | (2.22) | (1.01) |
| PT 4 | 11617 | 749 | 4414 | 7046.5 | 6002.5 | 11909 |
| | (1.02) | (15.85) | (2.69) | (1.64) | (1.98) | (1.00) |
| PT 5 | 11653.5 | 858.5 | 4381.5 | 7096.5 | 5973.5 | 11778.5 |
| | (1.02) | (10.91) | (2.77) | (1.72) | (1.99) | (1.02) |

NSB = Nonspecific binding; counts <100 consistent with saturation of transcobalamin proteins
Negative reference for IFBA; no binding to intrinsic factor (<1.11)
Positive reference for IFBA; binding to intrinsic factor (>1.43)
Indeterminate reference value (1.11 → 1.43)
Clinical Run = patients supernatant counts from UBBC and IFBA assays
DTPA = diethylenetriamine pentaacetic acid
CNB$_{12}$ = cyanocobalamin
MEB$_{12}$DTPA = methylcobalamin-b-(4-aminobutyl)-amide-DTPA
ADB$_{12}$DTPA = adenosylcobalamin-b-(4-aminobutyl)-amide-DTPA
CNB$_{12}$DTPA = cyanocobalamin-b-(4-aminobutyl)-amide-DTPA The IFBA assay demonstrated that DTPA does not significantly bind to IF (values less than the negative reference), whereas cyanocobalamin and the cobalamin-DTPA analogs do, in varying degrees, competitively inhibit Co-57 cyanocobalamin from binding to intrinsic factor. By using the counts of the Clinical run divided into the counts of the five solutions, the efficacy of binding to intrinsic factor can be estimated. The averaged percent binding of the five solutions to IF was: cyanocobalamin=92.5%; methylcobalamin-b-(4-aminobutyl)-amide-DTPA=63.2%; cyanocobalamin-b-(4-aminobutyl)-amide-DTPA=52.9%; adenosylcobalamin-b-(4-aminobutyl)-amide-DTPA=41.0% and 0.8% for DTPA. This is in contrast to the disclosure in Houts (U.S. Pat. No. 4,465,775) that the (b)-monocarboxylic acid of vitamin B$_{12}$ and its radio-iodinated derivative exhibit very low binding to IF.

Likewise the averaged percent binding of the five solutions to the transcobalamin proteins was: cyanocobalamin=100%, methylcobalamin-b-(4-aminobutyl)amide-DTPA=94.0%, adenosylcobalamin-b-(4-aminobutyl)amide-DTPA=90.4%, cyanocobalamin-b-(4-aminobutyl)amide-DTPA=66.4% and 3.6% for DTPA.

Thus, the attachment of DTPA to vitamin B$_{12}$ does alter its binding to the carrier proteins. As expected, non-labeled cyanocobalamin had the greatest affinity for IF and the transcobalamin proteins. Methylcobalamin-b-(4-aminobutyl)amide-DTPA was next, followed by adenosylcobalamin-b-(4-aminobutyl)amide-DTPA, and finally cyanocobalamin-b-(4-aminobutyl)amide-DTPA. There was also some nonspecific binding of DTPA to the carrier proteins (0.8% and 3.6%).

EXAMPLE 8

Chelation of Radionuclides

Under dim light, 1000 µg of methyl-, adenosyl-, and cyano-cobalamin-b-(4-aminobutyl)amide-DTPA were separately dissolved in 200 µl of normal saline. Next, 500 µCi of Indium-111 or 250 µCi of Gadolinium-153 were added to the cobalamin-DTPA solutions. The reactions were carried out at room temperature and room air. For the chelation of technetium, the dissolved cobalamin DTPA complexes were separately placed into sealed 2 ml vials. Next, 200 µl of stannous chloride solution (1000 µg/ml normal saline) were added to each vial. The vials were purged with nitrogen gas for 5 minutes. After this time, 1-5 mCi of Technetium-99m was added to the N$_2$ purged vials. Each vial underwent further nitrogen purging for 5 minutes. All chelation reactions were mixed gently for 5 minutes.

Control mixtures of 1000 µg of cyanocobalamin were dissolved in 200 µl of normal saline. Cyanocobalamin was mixed with Tc-99m at room temperature and room air, as well as within nitrogen purged vials containing 200 µl of the described stannous chloride solution. Additionally, the cobalamin-DTPA complexes underwent Tc-99m labeling in open vials at room air in the absence of the stannous chloride.

Specific activity was assessed by mixing 100 µl aliquots of methyl and adenosyl cobalamin-b-(4-aminobutyl)amide-DTPA (5 µg/100 µl normal saline) with 50 µl stannous chloride solution (1 µg/50 µl normal saline) in nitrogen purged 2 ml vials. Technetium-99m in 10, 25, 50, 75, and 100 mCi allotments of activity were added to the vials. The vials underwent gentle mixing and continuous nitrogen purging for five minutes after the addition of technetium.

Efficiency of chelation and specific activity were assessed via thin layer chromatography (TLC). Thin layer chromatographic strips (Grade 31 ET Chr-thickness 0.50 mm, flow rate (water) 225 mm/30 min, Whatman Lab Sales, Hilsboro, Oreg. 97123) were developed in acetone in dim light. The dry strips were placed on film (Ektascan-MC1, Eastern Kodak. Rochester, N.Y. 14650) for autoradiography (AR). Chromatographic and autoradiographic results were visually compared. All the radiolabeled cobalamin-DTPA complexes underwent TLC and AR to confirm 100% labeling prior to in vivo administration.

Under acetone development, free Tc-99m migrates to the top of the chromatographic strip, whereas In-111 and Gd-153 diffusely spread over the lower two-thirds of the strip. TLC and AR analysis demonstrated that there was 100% labeling of all three cobalamin-DTPA complexes with Tc-99m, In-111, and Gd-153. Specifically, all radioactivity was confined to the chromatographic distribution of the cobalamin analogues.

Since methyl and adenosyl cobalamin could potentially have greater uptake in malignant tissue, the chelation of Tc-99m, In-111, and Gd-153 by methyl and adenosylcobalamin-b-(4-aminobutyl)amide-DTPA underwent greater scrutiny. The chromatographic and autoradiographic images were consistently coincident. In contrast, unmodified cyanocobalamin did not demonstrate any affinity for binding the three radionuclides. As expected, there was minimal labeling of the cobalamin-DTPA complexes with Tc-99m in the absence of stannous chloride and hypoxic conditions.

At a concentration of 5 μg/100 μl the red color of the cobalamin-DTPA analogues is barely discernible in the aqueous state, and undetectable on TLC. However, the AR distribution is the same when compared to the more concentrated cobalamin analogue solutions with lower specific activity. Methyl and adenosyl cobalamin-b-(4-aminobutyl)amide-DTPA can chelate up to 50 mCi of technetium-99m per 5 μg with 100% efficiency. This results in a specific activity of 10 mCi/μg for the cobalamin-DTPA analogue.

EXAMPLE 9

In Vivo Studies

A. Biodistribution: Methylcobalamin-b-(4-aminobutyl) amide-DTPA in a concentration of 300 μg/100 μl normal saline was labeled with 3 mCi of Indium-111. The labeled vitamin $B_{12}$ analogue was diluted with normal saline to a final volume of 1000 μl. Via intraperitoneal injection (IP), five 12 week old female Balb-C mice (Harlan, Sprague, Dawley, Indianapolis. Ind. 46229) each received 200 μl (500 μCi) of the methylcobalamin-DTPA-$^{111}$In complex. For comparison, Indium-111-DTPA having the same concentration and specific activity of the methylcobalamin-DTPA analogue, was injected IP into three mice. All mice were sacrificed at 24 hours via $CO_2$ inhalation. The pancreas, spleen, kidneys, and heart were dissected in their entirety. A portion of the liver, lung, left quadricep muscle, and flank fat were also harvested. All tissue samples and organs were weighed wet, minced in 2.0 ml normal saline, and counted for five minutes in a gamma well counter (Minaxi Autogamma 5000, Packard Instrument, Downers Grove, Ill. 60515).

B. Gastrointestinal Absorption: Methylcobalamin-b-(4-aminobutyl)-DTPA and DTPA alone were labeled as described above, with the exception that the 3 mCi Indium/300 μg/100 μl normal saline solutions were not diluted. Two groups of three mice had a few drops of either [111]n-DTPA or methylcobalamin-b-(4-aminobutyl)-DTPA-In-111 placed in their oral cavities. The mice were sacrificed at 24 hrs, dissected, and studied as described above.

A modified Schillings test was performed on two mice. Specifically, each mouse received via subcutaneous and intraperitoneal administration, a 1000 μg loading dose of non-labeled methylcobalamin-b-(4-aminobutyl)amide-DTPA analogue. At 24 hrs, the mice were fed 2-3 drops of Indium-labeled methylcobalamin-b-(4-aminobutyl)amide-DTPA-complex. Urine and feces were collected from the three groups of mice after oral administration. The mice were sacrificed at 24 hours after ingestion of tracer and images and biodistribution data were obtained at that time.

C. Tumor Imaging: At 24 hours, there was a significant amount of adenosylcobalamin-b-(4-aminobutyl) amide-DTPA-In-111 uptake within the transplanted sarcoma both visually and by gamma well counting (Table II).

TABLE II

|  | Kidney | Liver | Spleen | Pancreas | Heart | Lung | Fat | Muscle | Tumor |
|---|---|---|---|---|---|---|---|---|---|
| Mouse 1 | 3717.5 | 943.3 | 433.1 | 304.2 | 134.7 | 130.9 | 101.4 | 93.6 | — |
| Mouse 2 | 3299.5 | 823.4 | 405.3 | 319.9 | 189.4 | 180.1 | 147.3 | 51.4 | — |
| Mouse 3 | 3462.7 | 768.6 | 366.8 | 310.3 | 171.2 | 113.1 | 102.8 | 43.9 | — |
| Mouse 4 | 224.0 | 56.9 | 44.1 | 13.4 | 10.3 | 6.2 | 12.6 | 5.4 | — |
| Mouse 5 | 130.2 | 41.5 | 26.2 | 13.0 | 6.9 | 6.0 | 19.5 | 5.6 | — |
| Mouse 6 | 281.6 | 66.1 | 57.7 | 14.1 | 12.5 | 10.5 | 18.8 | 5.0 | — |
| Mouse 7 | 621.4 | 126.4 | 67.8 | 40.0 | 35.0 | 38.4 | — | 13.6 | — |
| Mouse 8 | 700.5 | 111.7 | 66.6 | 39.3 | 29.8 | 51.2 | — | 12.4 | — |
| Mouse 9 | 601.7 | 115.8 | 66.3 | 41.2 | 31.3 | 40.6 | — | 12.0 | — |
| Mouse 10 | 119.4 | 24.0 | 19.5 | 6.0 | 5.6 | 5.4 | — | 8.9 | — |
| Mouse 11 | 117.3 | 25.5 | 19.0 | 6.7 | 5.0 | 5.3 | — | 2.6 | — |
| Mouse 12 | 110.1 | 23.2 | 18.1 | 5.9 | 4.8 | 5.0 | — | 3.7 | — |
| Mouse 13 | 4.3 | 0.82 | 0.67 | 0.75 | 0.54 | 1.1 | <BKG | <BKG | — |
| Mouse 14 | 4.1 | 0.80 | 0.70 | 0.76 | 0.54 | 0.33 | <BKG | <BKG | — |
| Mouse 15 | 3.1 | 0.73 | 0.65 | 1.1 | 0.50 | 0.44 | <BKG | <BKG | — |
| Mouse 16 | 0.64 | 0.28 | 0.62 | 0.93 | <BKG | <BKG | <BKG | <BKG | — |
| Mouse 17 | 0.54 | 0.21 | 0.67 | 0.96 | <BKG | <BKG | <BKG | <BKG | — |
| Mouse 18 | 0.59 | 0.30 | 0.48 | 0.61 | <BKG | <BKG | <BKG | <BKG | — |
| Mouse 19 | 3886.9 | 691.0 | 576.3 | 445.0 | 165.0 | 318.8 | 76.0 | 70.1 | 954.7 |
| Mouse 20 | 3115.6 | 464.8 | 309.5 | 242.7 | 134.8 | 230.0 | 170.4 | 81.9 | 1426.0 |
| Mouse 21 | 3592.8 | 675.0 | 478.3 | 439.0 | 157.8 | 335.2 | 198.0 | 166.5 | 1183.1 |
| Mouse 22 | 116.5 | 19.7 | 17.3 | 7.1 | 5.0 | 4.5 | 13.7 | 7.2 | 52.8 |
| Mouse 23 | 180.7 | 40.9 | 22.8 | 11.3 | 8.0 | 9.2 | 17.9 | 6.4 | 69.3 |
| Mouse 24 | 231.2 | 60.3 | 46.1 | 13.9 | 9.7 | 8.5 | 19.2 | 6.8 | 73.1 |
| Mouse 25 | 543.9 | 116.5 | 54.7 | 38.4 | 21.7 | 34.4 | 39.5 | 23.5 | 135.5 |
| Mouse 26 | 240.8 | 56.2 | 25.8 | 21.3 | 11.4 | 19.9 | 13.5 | 15.5 | 60.4 |
| Mouse 27 | 459.2 | 107.6 | 37.1 | 30.3 | 16.9 | 21.3 | 17.8 | 14.5 | 120.3 |
| Mouse 28 | 14.0 | 1.6 | 1.9 | 1.4 | 0.94 | 1.7 | 0.93 | .68 | 5.0 |

TABLE II-continued

|  | Kidney | Liver | Spleen | Pancreas | Heart | Lung | Fat | Muscle | Tumor |
|---|---|---|---|---|---|---|---|---|---|
| Mouse 29 | 9.9 | 1.3 | 1.4 | 8.2 | 0.61 | 0.87 | 0.75 | .60 | 2.8 |
| Mouse 30 | 10.2 | 1.4 | 1.6 | 3.1 | 0.85 | 0.93 | 0.79 | .63 | 3.4 |

Mice 1-3 and 19-21 = 500 μCi adenosylcobalamin-b-(4-aminobutyl)-amide-DTPA-$^{111}$In injected intraperitoneal
Mice 4-6 and 22-24 = 500 μCi DTPA-$^{111}$In injected intraperitoneal
Mice 7-9 = 500 μCi adenosylcobalamin-b-(4-aminobutyl)-amide-DTPA-$^{111}$In injected subcutaneously
Mice 10-12 = 500 μCi DTPA-$^{111}$In injected subcutaneously
Mice 13-15 = approximately 30 μCi methylcobalamin-b-(4-aminobutyl)-amide-DTPA-$^{111}$In administered orally
Mice 16-18 = approximately 30 μCi DTPA-$^{111}$In administered orally
Mice 25-27 = approximately 100 μCi methylcobalamin-b-(4-aminobutyl)-amide-DTPA-$^{111}$In tailvein injection
Mice 28-30 = approximately 100 μCi DTPA-$^{111}$In tailvein injection Despite the difference in the amount of activity injected between IP and IV routes, the degree of uptake within the tumor was consistently second behind the kidneys. The tumors had two to four times greater activity than the liver, spleen, and pancreas, with 4-12 times greater activity than that of the heart, lungs, fat, and muscle. As expected, no activity was seen to localize in the left flank of the control mice. Usual uptake in the liver and spleen was again seen. Gross pathology of the dissected masses demonstrated fat encapsulated tumors. Microscopically, by H & E stain, the tumors were solid masses of blue stained cells consistent with a sarcoma. No areas of necrosis were noted.

Although DTPA-$^{111}$In demonstrated uptake within the transplanted tumors, its concentration was 10-20 times less than that of adenosylcobalamin-DTPA-$^{111}$In.

D. Intravenous Administration: One milligram of either methyl or adenosylcobalamin-b-(4-aminobutyl)amide-DTPA was labeled with 5 mCi of $^{99m}$Tc as described above. Several mice were sacrificed via $CO_2$ inhalation at varying time intervals after tailvein injection. The first urine passed was collected and analyzed via TLC and AR.

E. Results

1. In Vivo Studies (a) Biodistribution

The organ and tissue distribution of the methyl and adenosylcobalamin-DTPA analogs at 24 hours was similar despite the route of administration (Table II). The kidneys were first, followed by the liver and spleen. The pancreas usually was next followed by the lungs, fat, heart, and muscle. The differences in activity between the pancreas, heart, lung, fat, and muscle was less significant after oral, subcutaneous, and intravenous administration. However, the ratio of uptake between the kidneys to liver, liver to spleen, and spleen to pancreas was relatively constant. The route of administration (IV, IP, PO) did not have any obvious effect on the chelation of Tc-99m or In-III by these complexes.

The greatest amount of DTPA-$^{111}$In uptake was in the kidneys. The distribution of DTPA was similar to the cobalamin analogs, especially after intraperitoneal injection. Despite their similarities, DTPA-$^{111}$In had 5-12 times less activity per organ or tissue sample when compared to the methyl and adenosylcobalamin analogs.

(b) Gastrointestinal Absorption

Methylcobalamin-b-(4-aminobutyl) amide-DTPA-In-111 was absorbed from the gastrointestinal tract after oral administration. The majority of activity was localized in the kidneys, liver, and spleen on delayed imaging. In the mice that were not "flushed" with oral and intraperitoneal doses of non-labeled methylcobalamin-b-(4-aminobutyl) amide-DTPA, no discernable activity was detected in the urine by gamma well counting. However, the mice that underwent the "modified Schillings test" had detectable radioactivity within their urine at one hour. Imaging at 24 hours of these "flushed" mice demonstrated significantly less activity throughout the body when compared to the "non-flushed" mice. Fecal radioactivity became detectable at 2 hours in both groups receiving the radioactive cobalamin analogs orally.

DTPA-$^{111}$In was also absorbed from the gastrointestinal tract, but to a lesser degree. No activity was detected in the heart, lungs, muscle, or fat tissue samples. Radioactivity was detected in urine and stool by two hours.

(c) Intravenous Administration

Micturition occurred at approximately 15 and 45 minutes after intravenous and intraperitoneal injections, respectively. The first passed urine after intravenous or intraperitoneal administration was always radioactive. TLC and AR analysis of the collected urine showed no evidence of dissociation of the Tc-99m or In-111 from the cobalamin-DTPA complexes. Images at 5 minutes and 4 hours after tailvein injection demonstrated focal early uptake in the kidneys which became obscured by the liver and spleen activity on the delayed images.

(d) Tumor Imaging

At 24 hours, there was a significant amount of adenosylcobalamin-b-(4-aminobutyl) amide-DTPA-In-111 uptake within the transplanted sarcoma both visually and by gamma well counting (Table II). Despite the difference in the amount of activity injected between IP and IV routes, the degree of uptake within the tumor was consistently second behind the kidneys. The tumors had two to four times greater activity than the liver, spleen, and pancreas, with 4-12 times greater activity than that of the heart, lungs, fat, and muscle. As expected, no activity was seen to localize in the left flank of the control mice. Usual uptake in the liver and spleen was again seen. Gross pathology of the dissected masses demonstrated fat encapsulated tumors. Microscopically, by H & E stain, the tumors were solid masses of blue stained cells consistent with a sarcoma. No areas of necrosis were noted.

Although DTPA-$^{111}$In demonstrated uptake within the transplanted tumors, its concentration was 10-20 times less than that of adenosylcobalamin-DTPA-$^{111}$In.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of imaging a tumor in a mammal comprising:
administering an effective amount of a compound of the formula:

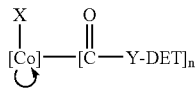

to the mammal, wherein the moiety

is cobalamin,

is a b-, d-, or e-carboxy residue of cobalamin; X is CN, OH, methyl, or adenosyl; Y is a linking group; DET is independently selected from a chelating group comprising a radionuclide and a chelating group comprising a paramagnetic metal ion; n is 2-3; or a pharmaceutically acceptable salt thereof; wherein each Y is independently selected from a divalent monomer, dimer, and trimer of —N(H)(CH$_2$)$_{2-6}$N(H)—.

2. A compound of the formula:

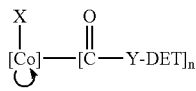

wherein the moiety

is cobalamin,

is a b-, d-, or e-carboxy residue of cobalamin; X is CN, OH, methyl, or adenosyl; Y is a linking group; DET is independently selected from a chelating group comprising a radionuclide and a chelating group comprising a paramagnetic metal ion; and n is 2-3; or a pharmaceutically acceptable salt thereof; wherein each Y is independently selected from a divalent monomer, dimer, and trimer of —N(H)(CH$_2$)$_{2-6}$N(H)—.

3. The compound of claim 2, wherein each DET is a chelating group comprising a radionuclide.

4. The compound of claim 3, wherein each radionuclide is independently selected from Antimony-124, Antimony-125, Arsenic-74, Barium-140, Beryllium-7, Bismuth-206, Bismuth-207, Cadmium-109, Cadmium-115, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Erbium-169, Europium-152, Gadolinium-153, Gold-195, Gold-199, Hafnium-175, Hafnium-175-181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium-95.

5. The compound of claim 4, wherein each radionuclide is independently selected from $In^{111}$, $Yt^{90}$, $Tc^{99}$, $Gd^{153}$, and $Re^{186}$.

6. The compound of claim 2, wherein each chelating group is independently selected from EDTA, DTPA, DOTA, TETA, and DCTA.

7. The compound of claim 6, wherein each chelating group is DTPA.

8. The compound of claim 2, wherein each Y is —N(H)(CH$_2$)$_4$N(H)—.

9. The compound of claim 2, wherein n is 2.

10. The compound of claim 2, wherein n is 3.

11. A met method of treating a tumor in a mammal comprising:
administering an effective amount of a compound of the formula:

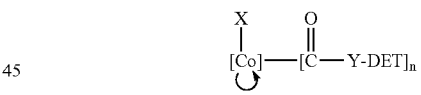

to the mammal, wherein the moiety

is cobalamin,

is a b-, d-, or e-carboxy residue of cobalamin; X is CN, OH, methyl, or adenosyl; Y is a linking group; DET is independently selected from a chelating group comprising a radionuclide and a chelating group comprising a paramagnetic metal ion; n is 2-3; or a pharmaceutically acceptable salt thereof; wherein each Y is independently selected from a divalent monomer, dimer, and trimer of —N(H)(CH$_2$)$_{2-6}$N(H)—.

12. The method of claim 1 or 11, wherein each DET is a detectable chelating group comprising a detectable radionuclide.

13. The method of claim 12, wherein each detectable radionuclide is independently selected from Antimony-124, Antimony-125, Arsenic-74, Barium-140, Beryllium-7, Bismuth-206, Bismuth-207, Cadmium-109, Cadmium-115, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Erbium-169, Europium-152, Gadolinium-153, Gold-195, Gold-199, Hafnium-175, Hafnium-175-181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium-95.

14. The method of claim 13, wherein the radionuclide is independently selected from In$^{111}$, Yt$^{90}$, Tc$^{99}$, Gd$^{153}$, and Re$^{186}$.

15. The method of claim 1 or 11, wherein each chelating group is independently selected from EDTA, DTPA, DOTA, TETA, and DCTA.

16. The method of claim 15, wherein each chelating group DTPA.

17. The method of claim 1 or 11, wherein each Y is —N(H)(CH$_2$)$_4$N(H)—.

18. The method of claim 1 or 11, wherein n is 2.

19. The method of claim 1 or 11, wherein n is 3.

20. The method of claim 1, comprising administering to the mammal a detectable amount of the compound in combination with a pharmaceutically acceptable vehicle, and detecting the presence of the compound in a tumor of the kidney, liver, pancreas, spleen, or gastrointestinal tract of the mammal.

21. The method of claim 11, comprising administering to the mammal an effective amount of the compound in combination with a pharmaceutically acceptable vehicle, and treating a tumor of the kidney, liver, pancreas, spleen, or gastrointestinal tract of the mammal.

22. The method of claim 20 or 21, wherein the administration is parenteral.

23. The method of claim 22, wherein the administration is intravenous.

24. The method of claim 23, wherein the administration is intraperitoneal.

25. The method of claim 20 or 21, wherein the administration is oral.

* * * * *

UNITED STATES PATENT AND TRADEMARK OFFICE
CERTIFICATE OF CORRECTION

PATENT NO. : 7,462,345 B2  Page 1 of 1
APPLICATION NO. : 11/603297
DATED : December 9, 2008
INVENTOR(S) : Douglas A. Collins It is certified that error appears in the above-identified patent and that said Letters Patent is hereby corrected as shown below:

Title Page, item (56); References Cited, U.S. Patent Documents, 5,057,301 after "Wilbur" please insert --et al.--;

Title Page, item (56); References Cited, U.S. Patent Documents, 5,372,808 after "Blatt" please insert --et al.--;

Column 1, line 11, please delete "Jul. 26. 2000" and insert --Jul. 26, 2000-- therefor;

Column 1, lines 14-15, please delete "09/059,277" and insert --09/059,227-- therefor;

Column 16, line 37 (Claim 11), before "method" please delete "met".

Signed and Sealed this

Fourteenth Day of July, 2009

JOHN DOLL
*Acting Director of the United States Patent and Trademark Office*